(12) United States Patent
Yanof et al.

(10) Patent No.: US 9,259,195 B2
(45) Date of Patent: Feb. 16, 2016

(54) REMOTELY HELD NEEDLE GUIDE FOR CT FLUOROSCOPY

(75) Inventors: Jeffrey H. Yanof, Solon, OH (US); Chris Bauer, Westlake, OH (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 2610 days.

(21) Appl. No.: 10/560,217

(22) PCT Filed: Jun. 17, 2004

(86) PCT No.: PCT/IB2004/002020
§ 371 (c)(1),
(2), (4) Date: Dec. 9, 2005

(87) PCT Pub. No.: WO2004/110242
PCT Pub. Date: Dec. 23, 2004

(65) Prior Publication Data
US 2006/0149147 A1    Jul. 6, 2006

Related U.S. Application Data

(60) Provisional application No. 60/479,576, filed on Jun. 18, 2003, provisional application No. 60/512,491, filed on Oct. 18, 2003.

(51) Int. Cl.
*A61B 5/05* (2006.01)
*A61B 6/12* (2006.01)
*A61B 17/34* (2006.01)
(Continued)

(52) U.S. Cl.
CPC ............... *A61B 6/12* (2013.01); *A61B 17/3403* (2013.01); *A61B 19/26* (2013.01); *A61B 19/22* (2013.01); *A61B 2017/00911* (2013.01); *A61B 2017/3405* (2013.01); *A61B 2019/5238* (2013.01)

(58) Field of Classification Search
USPC .......................................... 600/424, 427, 429
See application file for complete search history.

(56) References Cited

U.S. PATENT DOCUMENTS 3,893,813 A * 7/1975 Johnson ......................... 422/104
3,923,166 A * 12/1975 Fletcher et al. .................... 414/4
4,401,433 A * 8/1983 Luther .......................... 604/159
(Continued)

FOREIGN PATENT DOCUMENTS

DE    100 32 203 A1    1/2002
WO    99 37220 A1    7/1999
(Continued)

OTHER PUBLICATIONS

Stoianovici, et al.; PAKY Needle Driver; *URobotics*, Brady Urological Institute, Johns Hopkins Medical Institute; http://urology.jhu.edu/urobotics/projects/paky/; Jun. 11, 2003; pp. 1-4.

*Primary Examiner* — Nicholas Evoy

(57) ABSTRACT

A guide apparatus is provided for use with an associated imaging device to direct movement of an associated interventional implement relative to a patient disposed on the imaging device. A gripping area is adapted to the guide apparatus for manual gripping by an associated operator. A holding area is adapted to hold the associated interventional implement in an orientation suitable for motion relative to said patient along a selected linear path and also operative to translate the associated interventional implement along said selected linear path in response to manual force applied by the associated human operator at said gripping area.

20 Claims, 8 Drawing Sheets

(51) Int. Cl.
  *A61B 19/00* (2006.01)
  *A61B 17/00* (2006.01)

(56) References Cited

U.S. PATENT DOCUMENTS

| | | | | |
|---|---|---|---|---|
| 4,573,452 A * | 3/1986 | Greenberg | | 600/102 |
| 4,583,538 A * | 4/1986 | Onik et al. | | 606/130 |
| 4,733,661 A * | 3/1988 | Palestrant | | 606/108 |
| 5,053,042 A * | 10/1991 | Bidwell | | 606/130 |
| 5,078,140 A * | 1/1992 | Kwoh | | 600/417 |
| 5,142,930 A * | 9/1992 | Allen et al. | | 74/469 |
| 5,186,174 A * | 2/1993 | Schlondorff et al. | | 600/426 |
| 5,213,100 A * | 5/1993 | Summ | | 600/429 |
| 5,234,000 A * | 8/1993 | Hakky et al. | | 600/567 |
| 5,280,427 A * | 1/1994 | Magnusson et al. | | 600/407 |
| 5,397,323 A * | 3/1995 | Taylor et al. | | 606/130 |
| 5,441,042 A * | 8/1995 | Putman | | 600/102 |
| 5,494,034 A * | 2/1996 | Schlondorff et al. | | 600/425 |
| 5,564,436 A * | 10/1996 | Hakky et al. | | 600/567 |
| 5,568,593 A * | 10/1996 | Demarest et al. | | 700/247 |
| 5,584,292 A * | 12/1996 | Cheung | | 600/567 |
| 5,628,327 A * | 5/1997 | Unger et al. | | 600/562 |
| 5,647,373 A * | 7/1997 | Paltieli | | 600/567 |
| 5,950,629 A * | 9/1999 | Taylor et al. | | 128/897 |
| 5,957,933 A * | 9/1999 | Yanof et al. | | 606/130 |
| 6,035,228 A * | 3/2000 | Yanof et al. | | 600/429 |
| 6,064,904 A | 5/2000 | Yanof et al. | | |
| 6,245,028 B1 * | 6/2001 | Furst et al. | | 600/568 |
| 6,400,979 B1 | 6/2002 | Stoianovici et al. | | |
| 6,468,226 B1 * | 10/2002 | McIntyre, IV | | 600/564 |
| 6,487,431 B1 | 11/2002 | Iwano et al. | | |
| 6,488,667 B1 | 12/2002 | Murphy | | |
| 6,493,608 B1 * | 12/2002 | Niemeyer | | 700/302 |
| 6,665,554 B1 * | 12/2003 | Charles et al. | | 600/427 |
| 6,702,805 B1 * | 3/2004 | Stuart | | 606/1 |
| 6,785,572 B2 * | 8/2004 | Yanof et al. | | 600/427 |
| 6,853,856 B2 * | 2/2005 | Yanof et al. | | 600/417 |
| 7,206,626 B2 * | 4/2007 | Quaid, III | | 600/407 |
| 7,250,761 B1 * | 7/2007 | Marchione | | 324/300 |
| 8,444,631 B2 * | 5/2013 | Yeung et al. | | 606/1 |
| 9,060,792 B2 * | 6/2015 | Jaspers | | |
| 9,068,628 B2 * | 6/2015 | Solomon et al. | | |
| 2001/0027313 A1 * | 10/2001 | Shimmura et al. | | 606/1 |
| 2002/0087065 A1 * | 7/2002 | Yanof et al. | | 600/410 |
| 2002/0133174 A1 * | 9/2002 | Charles et al. | | 606/130 |
| 2003/0097060 A1 * | 5/2003 | Yanof et al. | | 600/424 |
| 2004/0106916 A1 * | 6/2004 | Quaid et al. | | 606/1 |
| 2006/0033707 A1 * | 2/2006 | Rodomista et al. | | 345/156 |
| 2006/0293643 A1 * | 12/2006 | Wallace et al. | | 606/1 |

FOREIGN PATENT DOCUMENTS

| | | |
|---|---|---|
| WO | WO 00/28882 A2 | 5/2000 |
| WO | WO 01/74259 A1 | 10/2001 |
| WO | 02 03878 A1 | 1/2002 |
| WO | 02 41782 A2 | 5/2002 |
| WO | 02 060653 A2 | 8/2002 |

* cited by examiner

REMOTELY HELD NEEDLE GUIDE FOR CT FLUOROSCOPY

CROSS REFERENCE TO RELATED APPLICATIONS

This application is filed under 35 U.S.C. 371 as a national stage entry of PCT/IB 04/002020, filed Jun. 17, 2004, which claims the benefit of U.S. provisional application Ser. No. 60/479,576 filed Jun. 8, 2003 and U.S. provisional application Ser. No. 60/512,491 filed Oct. 18, 2003, each of which is incorporated herein by reference.

The present invention relates to the art of interactive intra-procedural image-guided surgery and interactive pre-procedural surgical planning. It finds particular application in conjunction with the planning and implementation stages of minimally invasive stereotactic surgical procedures performed in CT imaging systems using a robotic localization device to orient an interventional implement such as a biopsy needle, ablation probe, or the like for planning and placement of objects or extraction of tissue from within the body of a patient, and will be described with particular reference thereto. It is to be appreciated, however, that the invention is also applicable to a wide range of imaging equipment and techniques, for example ultrasonic and magnetic resonance devices, and to a broad range of minimally invasive surgical procedures including many forms of surgery for placing objects at precise points within a patient such as interventional radiology procedures and for removing tissue from precise locations within the patient during ablation procedures and biopsies.

It is often desired that interventional medical procedures be as minimally invasive as possible. However, it is also desirable to be able to visualize or otherwise know the relative positions and/or orientations of surgical tools or devices with respect to surrounding anatomy. The latter goal may be achieved by a direct inspection of the anatomy. However, in the case of interior anatomy, direct inspection may be more invasive than desired insomuch as additional or larger incisions may have to be made to expose or access the interior anatomy for direct inspection.

For example, it is often desirable to sample or test a portion of tissue from human or animal subjects, particularly in the diagnosis and treatment of potentially cancerous tumors, pre-malignant conditions, and other diseases or disorders. Typically, in the case of tumors, when the physician suspects that cancer or an otherwise diseased condition exists, a biopsy is performed to determine if in fact cells from the tumor are cancerous or otherwise diseased. Many biopsies, such as percutaneous biopsies, are performed with a needle-like instrument used to collect the cells for analysis.

In recent years, the performance of interventional medical procedures such as needle biopsies has been enhanced by the use of x-ray imaging, CT scans, continuous CT (CCT), magnetic resonance imaging (1), fluoroscopy, single photon emission CT (SPECT), positron emission tomography (PET), and the like. The imaging equipment allows an interventionalist, such as a radiologist, surgeon, physician, or other medical personnel, to track the insertion of interventional devices, such as biopsy needles, in a subject during diagnostic and therapeutic procedures. While such imaging modalities allow procedures to be performed with minimal invasiveness and are helpful to the interventionalist and the patient, they have certain drawbacks.

For example, with some image-guided procedures, e.g., those using CT imaging, the tracking of the needle position is not done in real-time. That is to say, a static image is obtained and the needle position noted therein. Subsequently, the needle is advanced or retracted by a small amount and another static image obtained to verify the new needle position. This sequence is repeated as many times as necessary to track the needle's progression. Such a procedure tends to be time consuming insomuch as the needle progresses by only a short distance or increment between imaging, and needle progression is halted during imaging. Moreover, accuracy suffers to the extent that in the interim, i.e., between images, the needle's position cannot be visualized.

With the development of CCT imaging and fluoroscopy, real-time imaging has been made possible. In CCT scanning, a rotating x-ray source irradiates the subject continuously, generating images at a rate of approximately six frames per second. The use of CCT or fluoroscopy by the interventionalist for real-time guidance and/or tracking of the needle during biopsies is gaining popularity. As a result, biopsies have become not only more accurate, but also shorter in duration. However, because the imaging proceeds continuously, the patient and potentially the interventionalist are both exposed to a greater dose of radiation as compared to, e.g., non-continuous CT.

Accordingly, there exists in the prior art a trade-off between the level of radiation exposure experienced and real-time visualization of the procedure. That is to say, lower radiation exposure is conventionally achieved at the cost of real-time visualization, and conversely, real-time visualization is conventionally achieved at the cost of higher radiation exposure.

One problem resides in protecting the interventionalist from radiation exposure. In needle biopsies, for example, often the biopsy needle and guide are held within or close to the plane of the x-ray radiation so that the needle-tip will reside in the image plane thereby permitting continuous tracking. Staying close to the plane of imaging also, more often than not, allows for the distance the needle passes through the subject to be minimized. Consequently, this typically results in the interventionalist placing his/her hands in the x-ray beam. The hands of an interventionalist who performs several such procedures per day can easily receive a toxic dose of radiation. Therefore, it is desirable to provide interventionalists with a way to perform needle biopsies without the risk of radiation exposure.

A proposed approach to solving the aforementioned problem involves the use of automated robot-like mechanical systems which allow the interventionalist to manipulate the biopsy needle remotely while keeping hands clear of the x-ray beam. However, such systems typically reduce or eliminate the tactile sensations (e.g., pressure and tension forces, shear, and/or moment on the needle) otherwise available to an interventionalist directly manipulating the needle. This is disadvantageous in that interventionalists typically obtain useful information from these tactile sensations and rely upon it regarding the procedure. For example, they are often able to feel the progress of the needle as it transitions between different tissue types, makes contact with bones, punches through skin, etc. The interventionalists generally desire this "feel" as they perform biopsies. To trained personnel, it serves as an additional indication of the needle's location.

Commonly owned U.S. Pat. No. 6,245,028 to Furst, et al. addresses the lack of feel and interventionalist radiation exposure issues in part. However, the tubular curved needle guide disclosed there encloses the biopsy needle and does not provide a means of lateral release. It is also not clear if the needle could be driven on a straight path or how the interventionist could make manual adjustments to steer the needle such as, for example, by beveling the tip of the needle should the need arise. In some embodiments of the needle biopsy system disclosed there, a master-slave system is used wherein a joystick controlled motorized device drives the needle. Failure modes or mechanisms are not discussed in either the drive mechanism or in the simulated force feedback system.

The present invention contemplates a new and improved interactive image-guided interventional method and system including a remotely held needle guide apparatus for enabling radiologists to safely extend their reach into the active region of a CT aperture during needle insertion under real-time x-ray CT fluoroscopy. The present invention overcomes the above-referenced problems arising in the prior art techniques and others as will become apparent to those skilled in the art.

In accordance with one aspect of the present invention, a guide apparatus is provided for use with an associated imaging device to direct movement of an associated interventional implement relative to a patient disposed on the imaging device. The guide apparatus includes a connector portion for coupling the guide apparatus with the associated imaging device, a main body portion, a gripping area, and a holding area. The main body portion is supported relative to the associated imaging device by the connector portion. The gripping area is formed at a first end of the main body portion and is adapted for manual gripping by an associated human operator of the subject guide apparatus. The holding area is formed at the second end of the main body portion and is adapted to hold the associated interventional implement in an orientation suitable for motion relative to the patient along a selected linear path. The holding area is operative to translate the associated interventional implement along the selected linear path in response to manual force applied by the associated human operator at the gripping area.

In accordance with another aspect of the invention, a system is provided for inserting a medical device into a patient. The system includes an imaging device scanning the patient to generate a volumetric image data set of the patient. A human readable display device is provided for displaying an image of the patient derived from the volumetric image data set. Means are provided for selecting a virtual trajectory defining a path for inserting the medical device into the patient. Robotic means are provided on the imaging device, the robotic means being movable into selected positions relative to the imaging device. A guide apparatus is disposed on the robotic means, the guide apparatus being adapted to direct movement of the medical device relative to the patent.

In accordance with yet a further aspect of the invention, the imaging device is a CT scanner, an MRI scanner, a CCT scanner, a fluoroscope, a SPECT scanner, a PET scanner, or a combination of the foregoing.

In accordance with yet a further aspect of the invention, the medical device is a tissue ablation probe or a biopsy needle.

In accordance with a still further aspect of the invention, the guide apparatus includes a connector portion having a linear slide joint for movement of the guide apparatus along a single linear trajectory.

One advantage of the present invention is that it guards against excessive radiation exposure to both the interventionist and the patient.

Another advantage of the present invention is that it provides tactile feedback to the interventionist.

Yet another advantage of the present invention is that it permits the interventionist to continually monitor and/or visualize the progression of the procedure via a virtual view of the same while continuously obtaining real-time images of the actual procedure for verification.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating preferred embodiments and are not to be construed as limiting the invention.

Figure 1:
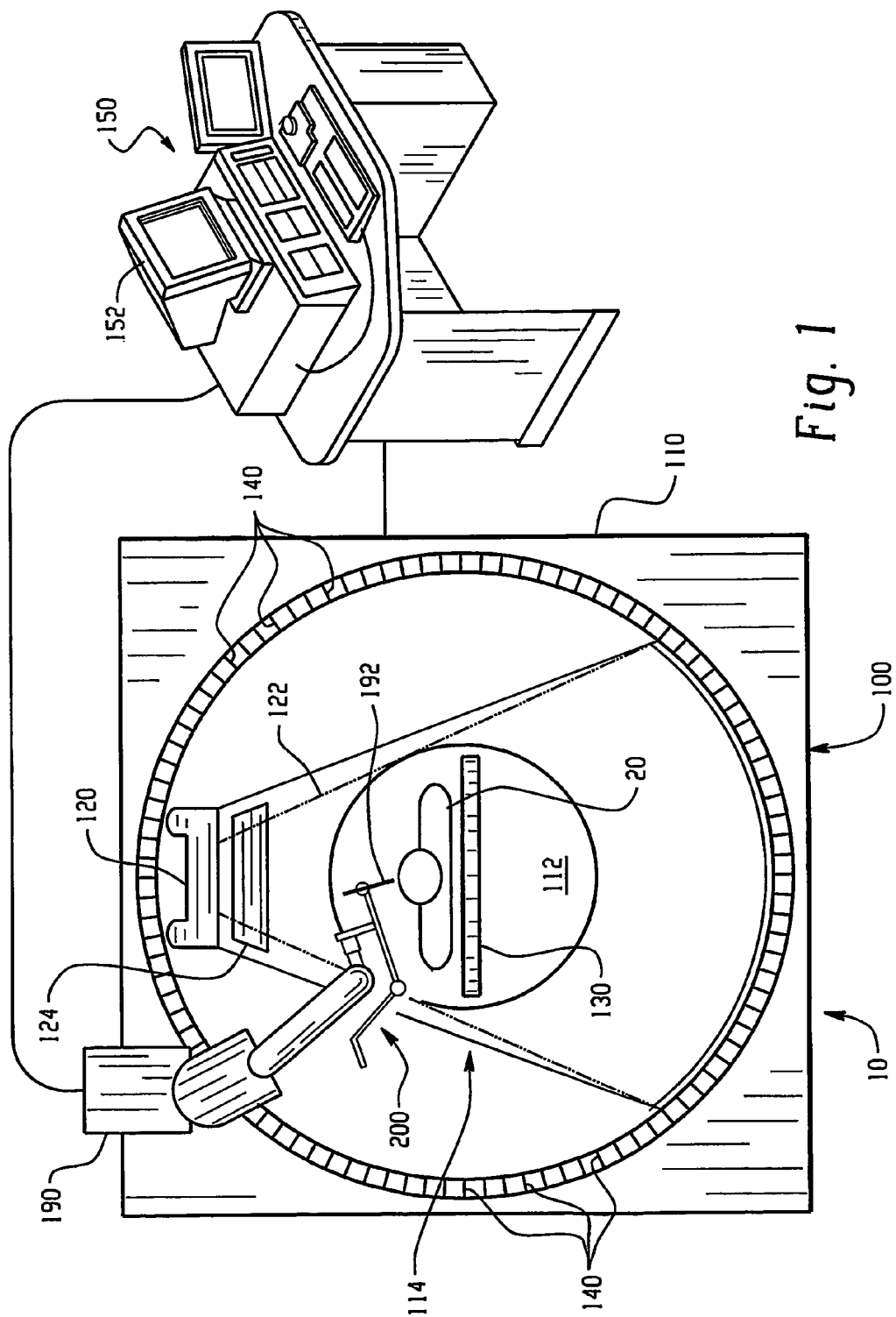
FIG. 1 is a diagrammatic illustration of an image-guided interventional medical procedure system in accordance with aspects of the present invention.
Figure 2:
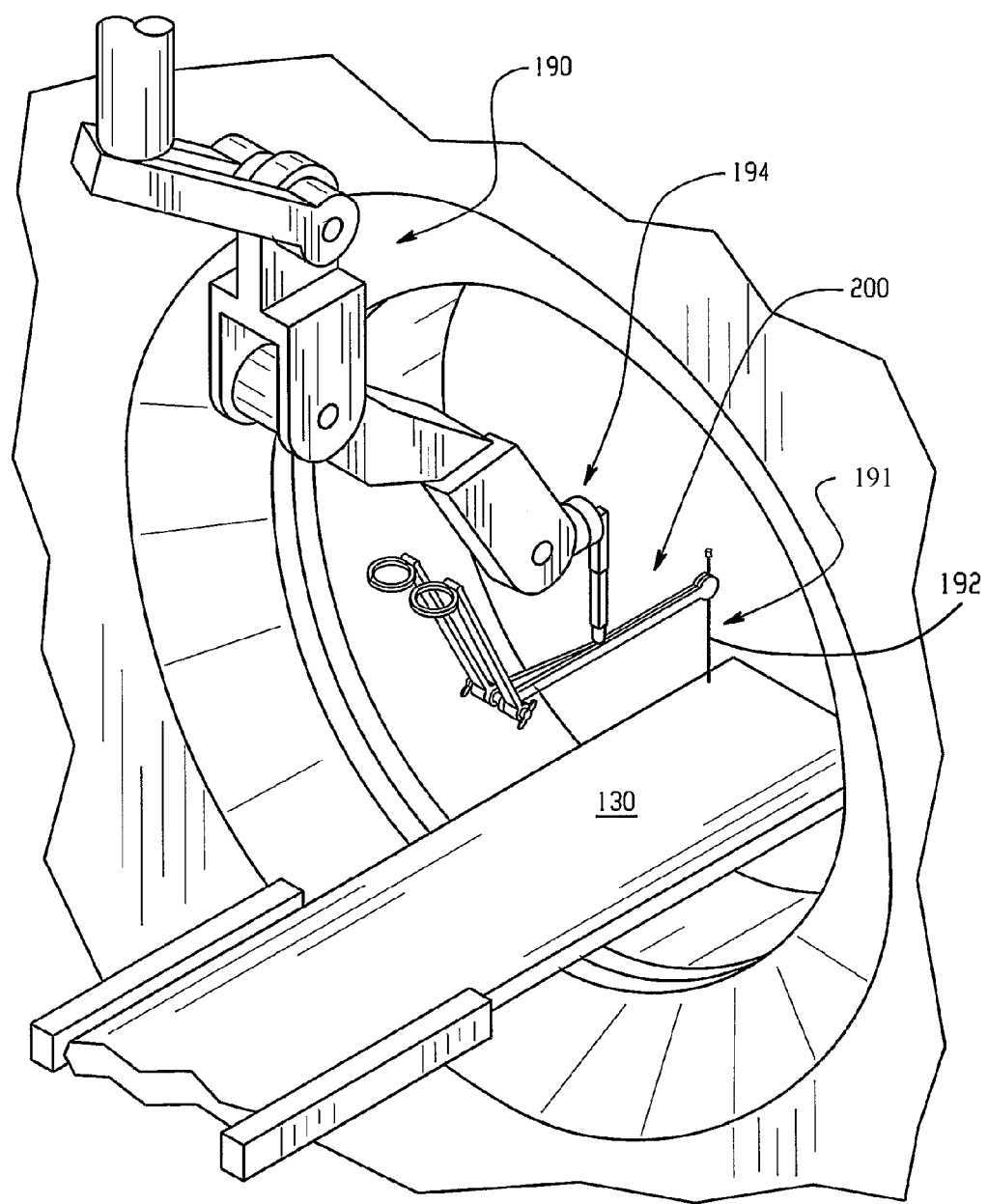
FIG. 2 shows a robotic arm supporting a remotely held needle guide apparatus carrying a biopsy needle in accordance with aspects of the present invention.

With reference to FIG. 1, an image-guided interventional medical procedure system 10 includes a diagnostic imaging apparatus 100 capable of generating medical diagnostic images of a subject 20. Optionally, the imaging apparatus 100 is an x-ray imaging device, CT scanner, CCT scanner, MRI scanner, fluoroscope, SPECT scanner, PET scanner, a combination of the foregoing or the like.

In the illustrated preferred embodiment, the diagnostic imaging apparatus 100 is a CT scanner having a stationary gantry 110 which defines a central examination region 112. A rotating gantry 114 is mounted on the stationary gantry 110 for rotation about the examination region 112. A source of penetrating radiation 120, such as an x-ray tube, is arranged on the rotating gantry 114 for rotation therewith. The source of penetrating radiation produces a beam of radiation 122 that passes through the examination region 112 as the rotating gantry 114 rotates. A collimator and shutter assembly 124 forms the beam of radiation 122 into a thin fan-shape and selectively gates the beam 122 on and off. Alternately, the radiation beam 122 is gated on and off electronically at the source 120. Using an appropriate reconstruction algorithm in conjunction with the data acquired from the CT scanner, images of the subject 20 therein are selectively reconstructed.

A subject support 130, such as an operating table, couch or the like, suspends or otherwise holds the subject 20 received thereon, such as a human or animal patient, at least partially within the examination region 112 such that the thin fan-shaped beam of radiation 122 cuts a cross-sectional slice through the region of interest of the subject 20.

In the illustrated fourth generation CT scanner, a ring of radiation detectors 140 is mounted peripherally around the examination region 112 on the stationary gantry 110. Alternately, a third generation CT scanner is employed with an arc of radiation detectors 140 mounted on the rotating gantry 114 on a side of the examination region 112 opposite the source 120 such that they span the arc defined by the thin fan-shaped beam of radiation 122. Regardless of the configuration, the radiation detectors 140 are arranged to receive the radiation emitted from the source 120 after it has traversed the examination region 112.

In a source fan geometry, an arc of detectors which span the radiation emanating from the source 120 are sampled concurrently at short time intervals as the source 120 rotates behind the examination region 112 to generate a source fan view. In a detector fan geometry, each detector is sampled a multiplicity of times as the source 120 rotates behind the examination region 112 to generate a detector fan view. The paths between the source 120 and each of the radiation detectors 140 are denoted as rays.

The radiation detectors 140 convert the detected radiation into electronic projection data. That is to say, each of the radiation detectors 140 produces an output signal which is proportional to an intensity of received radiation. Optionally, a reference detector may detect radiation which has not traversed the examination region 112. A difference between the magnitude of radiation received by the reference detector and each radiation detector 140 provides an indication of the amount of radiation attenuation along a corresponding ray of a sampled fan of radiation. In either case, each radiation detector 140 generates data elements which correspond to projections along each ray within the view. Each element of data in the data line is related to a line integral taken along its corresponding ray passing through the subject being reconstructed.

Figure 5:
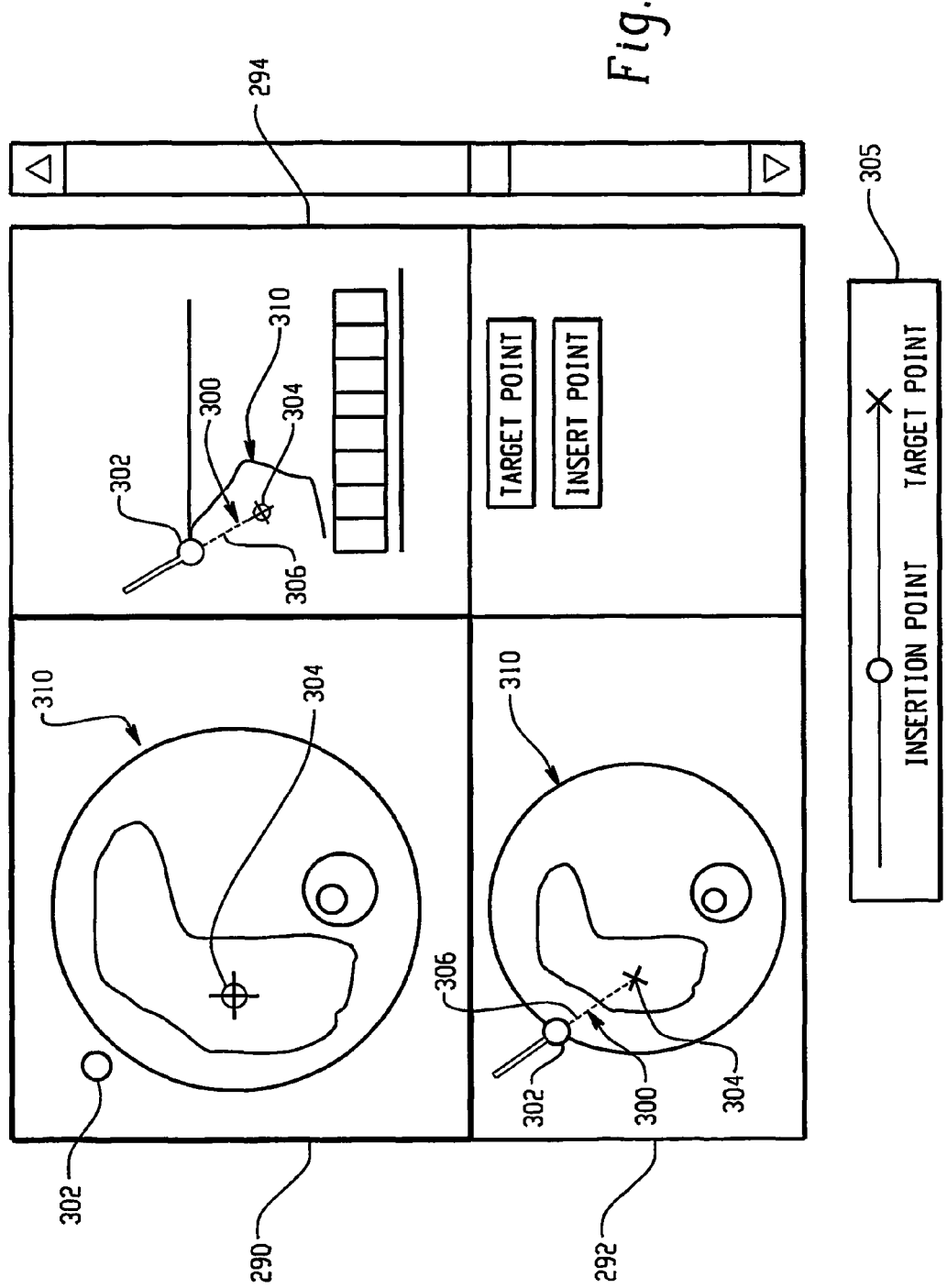
FIG. 5 is a virtual planning view in accordance with aspects of the present invention for interventional medical procedures; and, FIG. 6 is a block diagram showing the preferred operation of the image-guided interventional medical procedure system in accordance with aspects of the present invention.

With each scan by the CT scanner, the image data from the radiation detectors 140 is collected and reconstructed into image representations of the subject 20 in the usual manner. For example, a data processing unit incorporated in a workstation and/or control console 150 collects the image data and reconstructs the image representation therefrom using rebinning techniques, convolution/backprojection algorithms, and/or other appropriate reconstruction techniques. In a preferred embodiment, the image representations corresponding to the cross-sectional slice traversed by the thin fan-shaped beam of radiation 122 through the region of interest of the subject 20, are displayed on a human viewable display, such as a video monitor 152 or the like, which is also part of the console 150. Several preferred views are illustrated in FIG. 5 and will be described in greater detail below. The control console 150 is optionally remotely located with respect to the imaging apparatus 100 (e.g., in a shielded room adjacent the scanning room containing the imaging apparatus 100) and typically it includes one or more monitors 152, a computer or data processing hardware and/or software, one or more memories or other data storage devices, and one or more standard input devices (e.g., keyboard, mouse, trackball, etc.).

Figure 3:
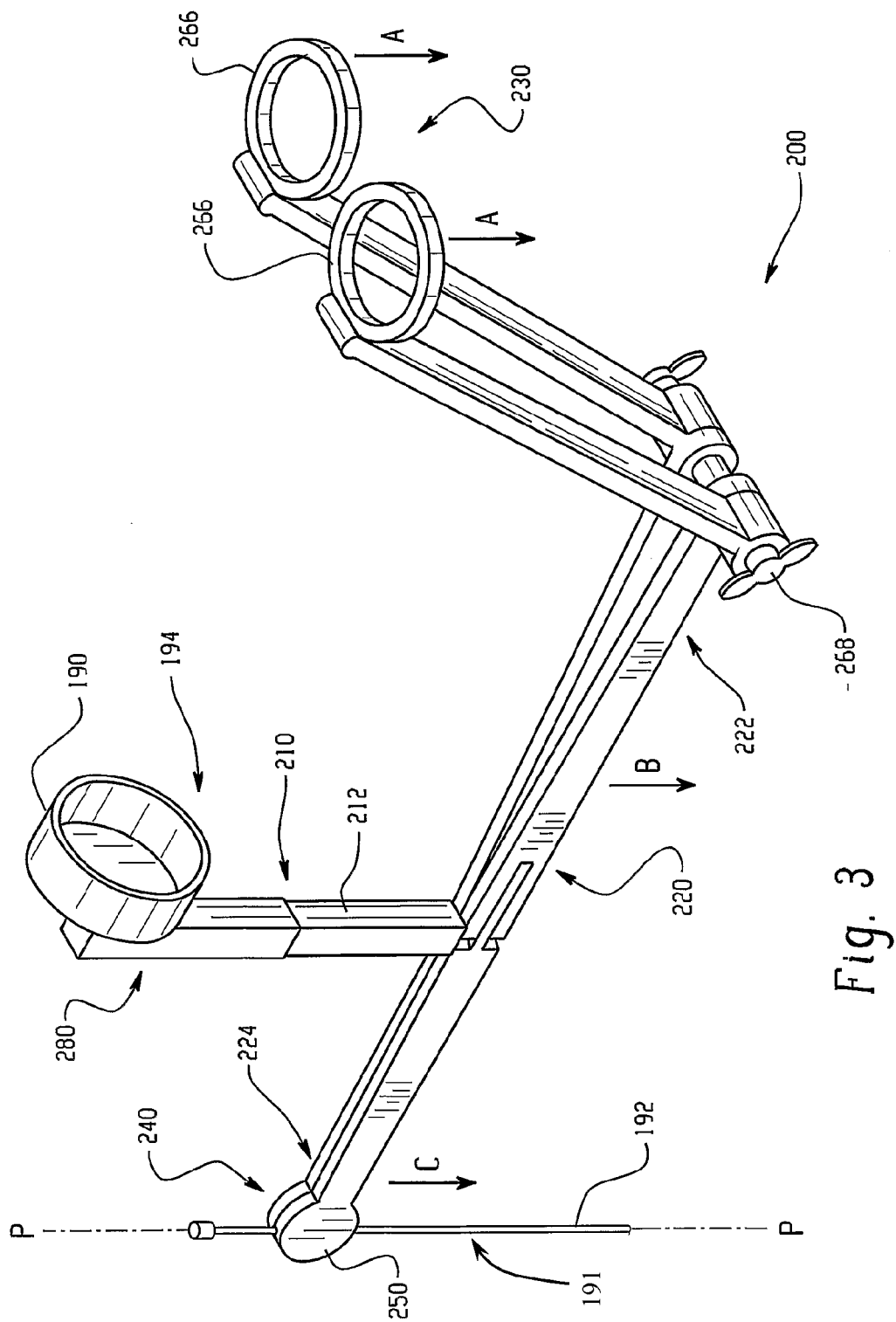
FIG. 3 is a perspective view showing the remotely held needle guide apparatus formed in accordance with aspects of the present invention.

With reference to FIGS. 2-4B, and continuing reference to FIG. 1, in a preferred embodiment, the image-guided interventional medical procedure system 10 also includes a robotic arm 190 preferably carried on the stationary gantry 110. The robotic arm 190 supports a remotely held needle guide apparatus 200 carrying an interventional implement or other like medical device 191 e.g., an ablation probe or a biopsy needle 192 at a desired location and trajectory. The medical device 191 is supported within the examination region 112 as shown. The robotic arm 190 is preferably a fully adjustable multi-jointed multi-segmented arm with each joint having at least one degree of freedom. As will be described in greater detail later herein, a medical device 191, preferably the ablation probe or biopsy needle 192, is held by the needle guide apparatus 200 (as best seen in FIG. 3). Accordingly, by appropriately arranging the robotic arm 190 (i.e., flexing or otherwise adjusting the multiple joints and/or segments, but preferably by executing a program which aligns the arm to the planned trajectory) and by appropriately positioning the subject 20 and the robotic arm 190 relative to one another, any arbitrary position and/or orientation of the biopsy needle 192 relative to the subject 20 is achieved as desired. Preferably, the position and/or orientation of the medical device 191 defines a physical path coincident with the virtual planned trajectory.

With particular reference to FIG. 3, the remotely held needle guide apparatus 200 includes a connector portion 210 for coupling the guide apparatus 200 with the associated imaging device 100, preferably to the distal end 194 of the robotic arm 190. In its preferred form, the connector portion 210 includes a prism joint linear slider mechanism 212 having a single degree of freedom.

A main body portion 220 of the needle guide apparatus 200 is supported relative to the associated imaging device 100 by the connector portion 210. A gripping area 230 is formed at a first end 222 of the main body portion 220. The gripping area 230 is provided to adapt the needle guide apparatus 200 for manual gripping by an associated interventionist. A medical device holding area 240 is formed at a second end 224 of the main body portion 220 as illustrated. The holding area 240 is adapted to hold an associated interventional implement such as a biopsy needle 192 in an orientation suitable for motion relative to the patient 20 along a selected linear path P. The implement holding area 240 is operative to translate the associated interventional tool 192 such as an ablation probe or a biopsy needle 192 along a linear path, selected in a manner to be described in greater detail below, in response to manual force provided by the associated interventionist at the gripping area 230. In that manner, force applied by the interventionist at the gripping area 230 in the direction A urges the main body portion 220 to translate along a linear path B as constrained by the single degree of freedom connector portion 210. This in turn causes the holding area 240 to similarly move in a linear path C. It is to be appreciated that each of the linear paths A, B, and C traversed by portions of the needle guide apparatus 200 lie or extend in parallel with the path defined by the single degree of freedom connector portion 210. The connector portion 210 is preferably a linear slider prism joint although any suitable mechanism which restrict movement to a single linear path could be used as well.

In connection with the above, it is further to be appreciated that, preferably, the associated interventional implement 192 is held in a relationship relative to the patient disposed on the patient support along a linear path P which lies identically parallel with the linear paths A, B, and C traversed by the needle guide apparatus 200 as constrained by the linear slider prism joint 212. To that end, the holding area 240 includes a needle holder portion 250 which is adapted to hold the implement 192 in an orientation suitable for motion relative to the patent 20 along the planned trajectory P. Preferably, the needle holder portion 250 is biased in an open position by the gripping area 230 or through other means so that the needle 192 is held firmly in place only through the active participation of the interventionist. In that sense, the needle holder 250 formed in the holding area 240 is "failsafe" and preferably releases from the grip of the guide apparatus 200 when active physical control over the apparatus is discontinued by the interventionist. Prior art systems such as robotic or other direct mechanical needle feeding apparatus do not enjoy this benefit and therefore pose a potential risk to the patient. At least a substantial portion of the needle holder 250, and part of the second end 224 as desired, is preferably formed of an x-ray transmissive material to prevent scattering for easier visualization of the interventional process. An acrylic material is preferred for use in the needle holder area of the subject apparatus. However, any other suitable easily sterilizable x-ray transmissive material can be used as desired. Also, the needle holder 250 may be coated with an x-ray transmissive material to enhance the grip of the holder on the tool 192 as desired.

Figure 3B:
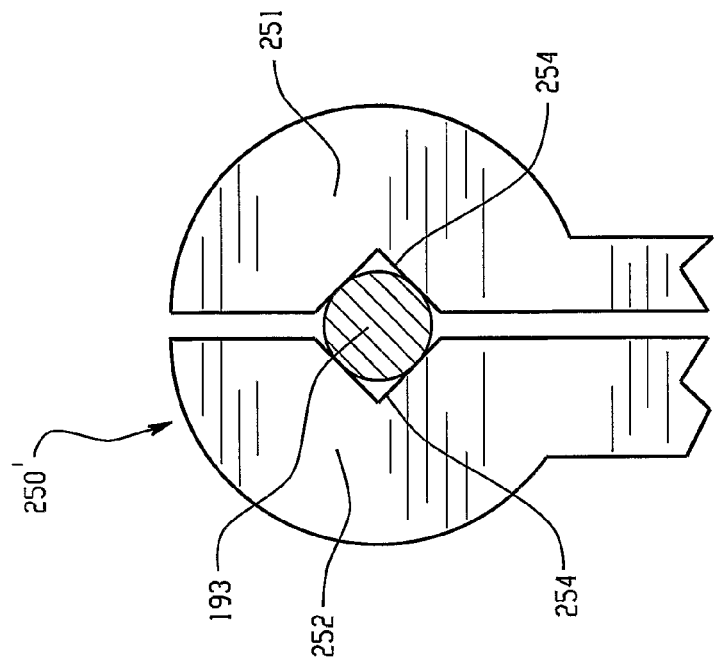
FIGS. 3A and 3B are elevational views showing a preferred embodiment of a needle holder portion of the needle guide device of FIG. 3.
Figure 3A:
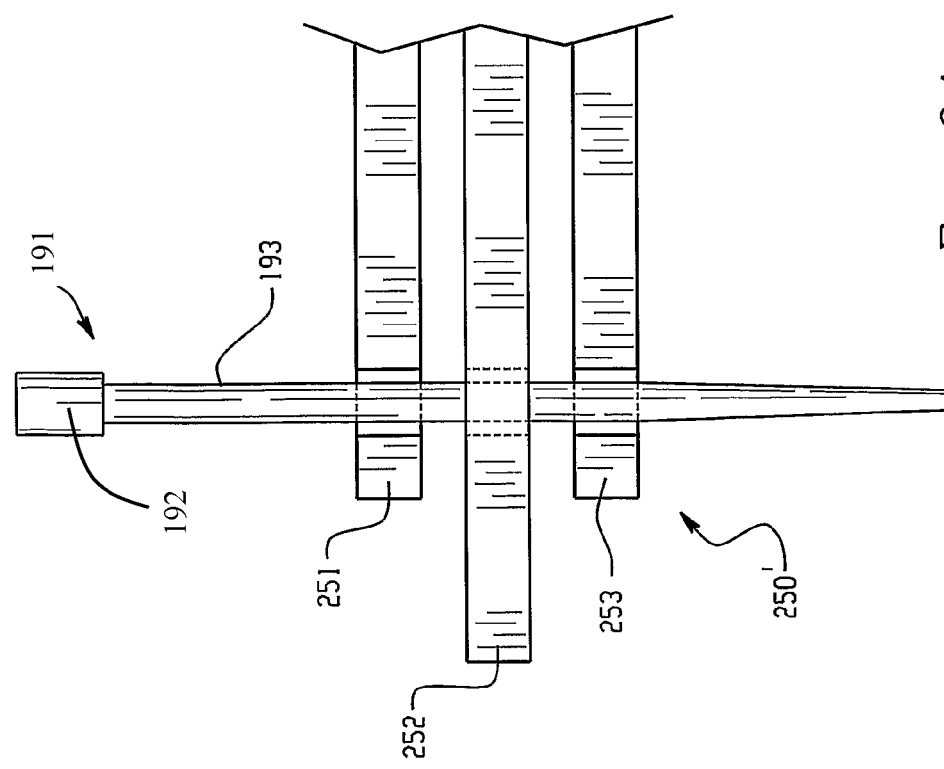

FIGS. 3A and 3B show an alternative preferred embodiment of the subject needle holder 250' including a set of tweezers-like arm portions 251, 252, and 253 adapted to grip the needle portion 193 of the biopsy needle 192 in a V-shaped groove 254 formed thereby. It is to be appreciated that the V-shaped groove enables needles or probes having a variety of diameters to be held by the holder while maintaining a single common central axis line relative to the needle guide apparatus 200. Although three arm portions are shown, more arms having a similar configuration can be used as well for added precision and stability. In the form shown, the uppermost arm portion 251 and the lowermost arm portion 253 are adapted to engage the needle 193 on an opposite side from the central arm portion 252. Each of the arm portions overlie each other in the vertical, or needle, direction so that the confronting arm portions can overlap in the vertical direction without mechanically interfering with each other for grasping needles having a small diameter. For larger needles, the arm portions 251-253 do not overlap while in the grasped orientation, but rather engage the needle 193 at linear contact points established by the V-groove areas 254 such as illustrated in FIG. 3B.

Figure 4A:
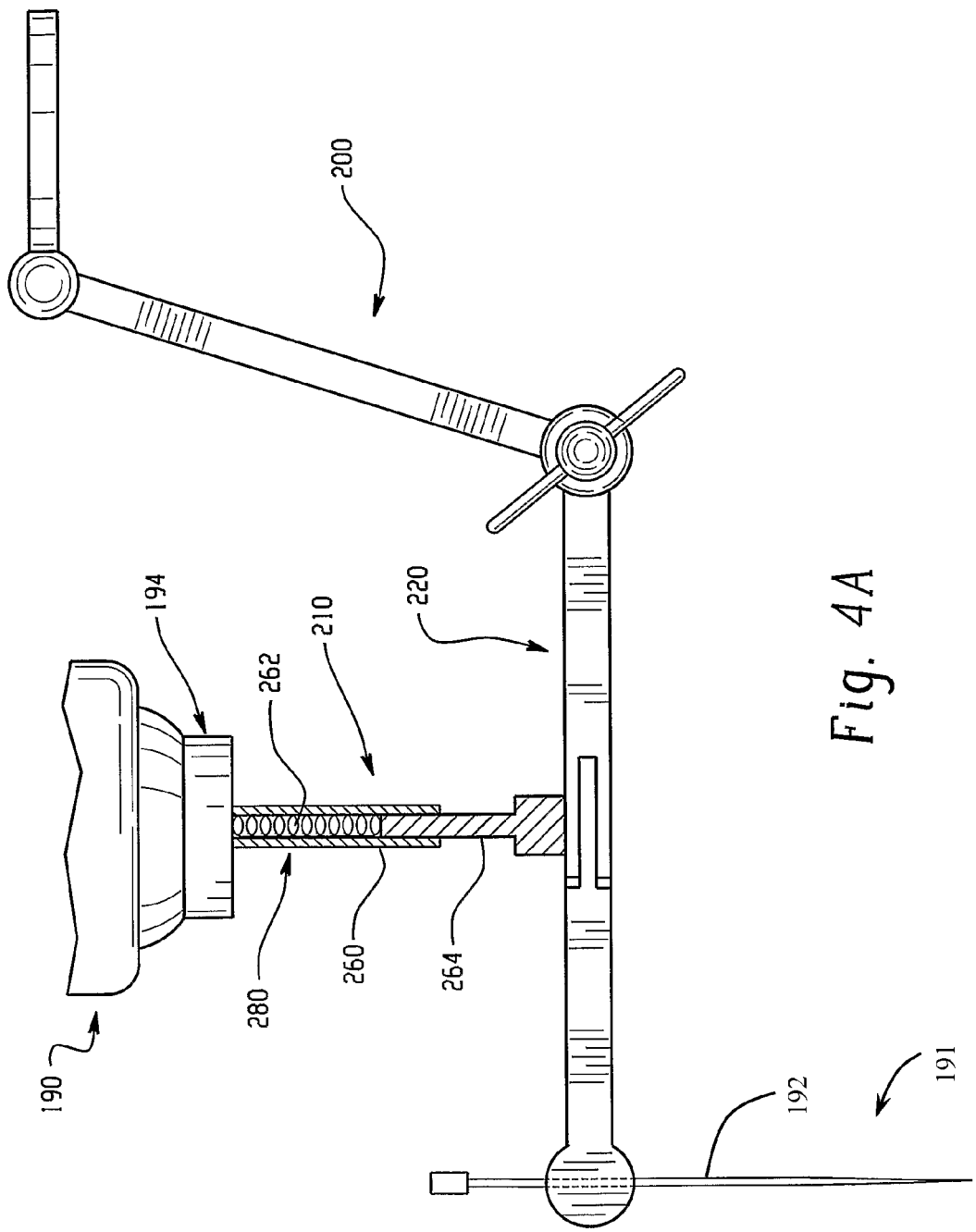
FIGS. 4A and 4B are partial cross-sectional views of a linear guide mechanism of the remotely held needle guide apparatus of FIG. 3.

FIG. 4A illustrates a cross-sectional view of the connector portion 210 of the subject guide apparatus 200. In the embodiment illustrated, the connector portion 210 includes a linear slider 260 including an internal spring mechanism 262 to bias a lower end 264 of the connector portion supporting the main body 220 of the apparatus 200 against gravity relative to the distal end of the robot arm 190. In its preferred form, the spring mechanism 262 has adequate spring force to compensate for the overall weight of the guide apparatus 200. In that way, the guide apparatus is held in an unextended position until the interventionist actively pushes downwardly on the holding area 230. Preferably, as illustrated in FIG. 3, the holding area 230 includes a set of stirrup-like handles 266 held in a selectable angular relationship relative to the first end 222 of the main body portion 220. A set of large wing-nuts 268 or the like are provided for adjustment for ease and convenience of use.

Figure 4B:
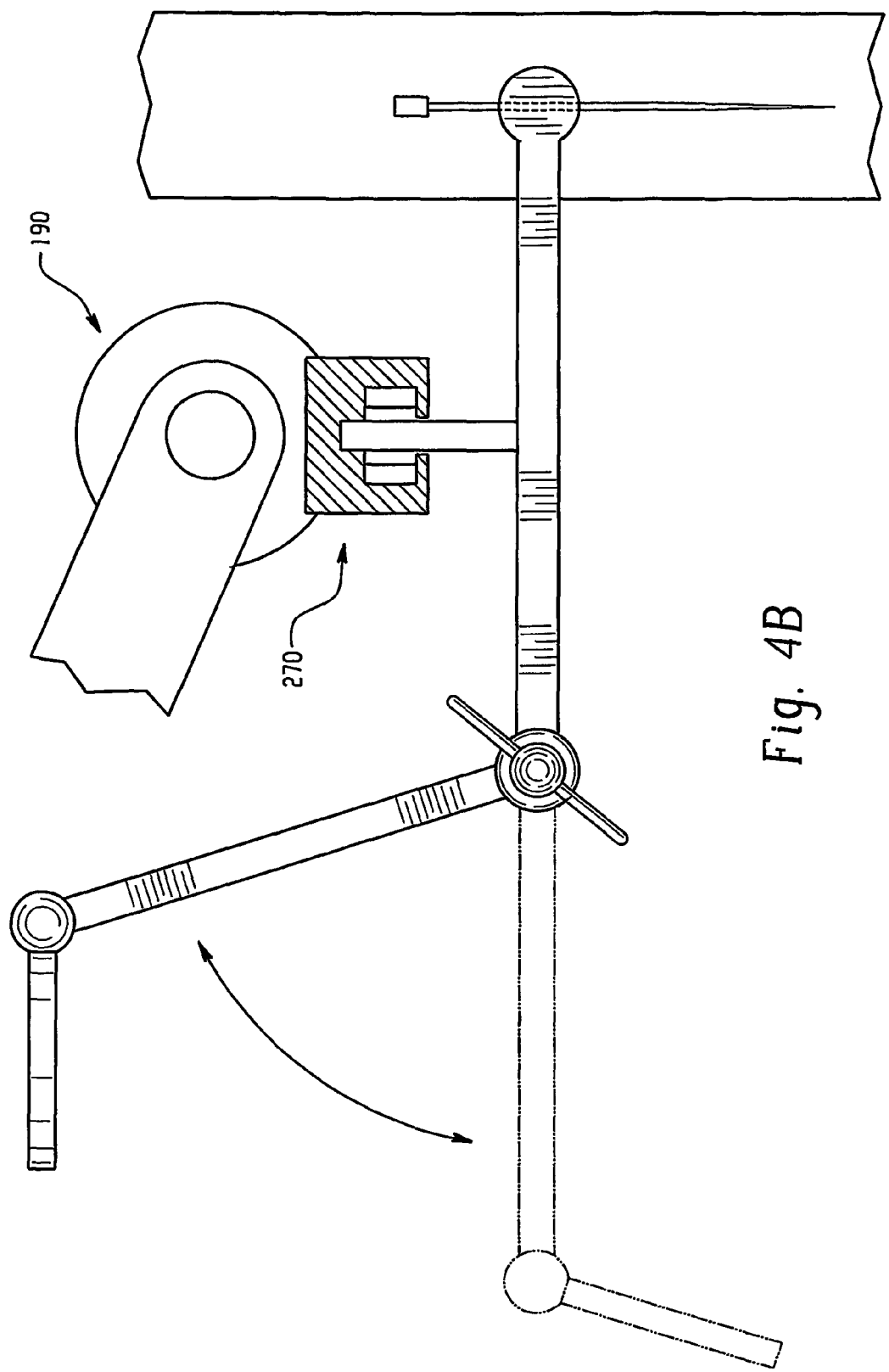

FIG. 4B shows a cross-sectional view of another embodiment of the subject connector portion 210 in the form of a prism joint 270. As with the linear slide joint 260 discussed above, the prism joint 270 permits only single degree of freedom movement. Thus, the joint provides for translation of the apparatus 200 and of the interventional biopsy needle 192 only along the planned trajectory P.

Preferably, in each of the connector areas 210 described above, a position feedback device 280 is provided for deriving a virtual display of the location of the biopsy needle 192 relative to the patient during an interventional procedure such as shown in FIG. 5. To that end, as the surgeon exerts manual force against the holding area of the apparatus, the needle is driven into the patient and feedback of needle movement relative to the distal end of the robot arm is provided to the scanner by the feedback device. Preferably, a resolver is provided using a gear connection or the like disposed between the fixed and movable parts of the apparatus 200. However, a slide scale, linear wiper, or other such device can be used as well.

In accordance with a preferred embodiment, a diagnostic medical image or images of the region of interest of the subject 20 are obtained prior to conducting the interventional medical procedure. For example, where the procedure of interest is a tissue ablation procedure or a biopsy, pre-procedural or pre-operative images are obtained including axial slices or views which contain or are near the tumor or diseased anatomy. Optionally, the pre-operative images or image data is obtained with the imaging apparatus 100, or another diagnostic medical imaging device. Using the pre-operative image data, the interventionalist or other medical personnel plan the procedure via a virtual procedure planning system and/or method. The preferred example of virtual procedure planning is found in commonly owned U.S. Pat. No. 6,064, 904 to Yanof, et al. which is included herein.

With reference to FIG. 5, the virtual procedure planning results in an image or images of the region of interest including superimposed therein a virtual surgical instrument, e.g., a virtual ablation probe or a virtual biopsy needle 300, which is moved on the screen using a mouse pointer or the like to desired orientation and position relative to the pre-operative images obtained. That is to say, the pre-operative images visualize the anatomy of interest 310, and via the virtual planning, a virtual needle 300 or other medical instrument is superimposed or otherwise incorporated therein at the desired position and trajectory for carrying out the procedure. In the illustrated embodiment, the virtual needle 300 is defined by an entry or percutaneous insertion point 302, a target point 304 and/or depth-to-target reading 305, and a needle trajectory 306 connecting the two points and/or an angulation reading. Collectively, the pre-operative or pre-procedural images with the virtual surgical or medical instrument depicted therein are referred to herein as the virtual and/or planning views 290-294. In a preferred embodiment, the virtual planning views include the virtual needle 300 superimposed on a transverse axial slices or oblique plane containing the needle's trajectory. Using multi-planar reformatted (MPR) views, the needle's trajectory 306 is tracked in the virtual planning view regardless of whether or not it is in the transverse axial plane. That is to say, the virtual planning view is optionally generated from volumetric data and it can therefore show the complete trajectory of the virtual needle 300 for any arbitrary orientation, unlike the actual images generated by the CT scanner which can for the most part only readily obtain images of the transverse axial view. Accordingly, where the needle trajectory is not co-planar with the transverse axial view, visualization of the complete needle trajectory is not lost.

The virtual planning views are preferably loaded and/or maintained on the workstation or control console 150, or alternately, it is maintained on a separate computer, workstation or console from which it may be displayed and/or viewed by the interventionalist.

Figure 6:
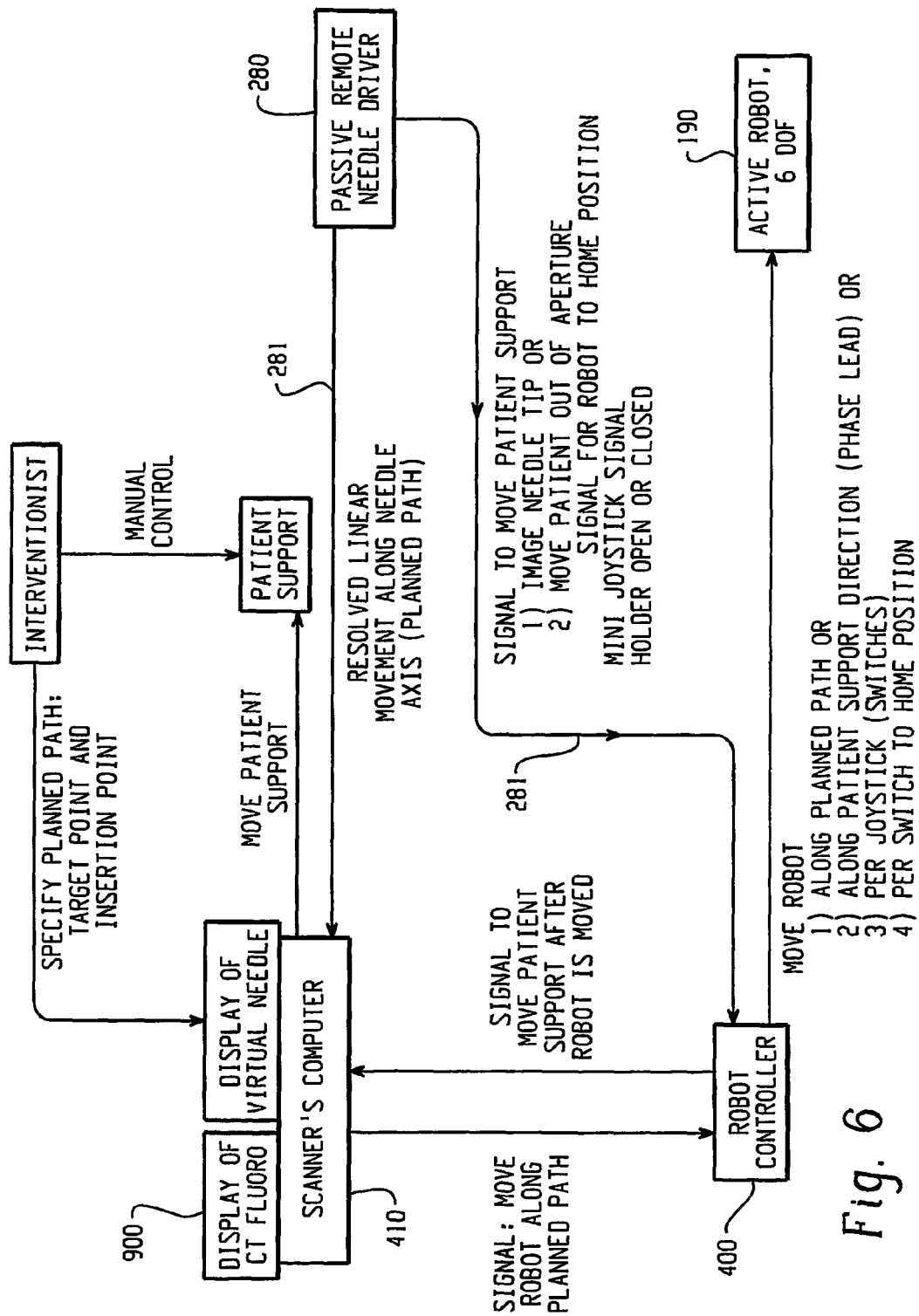

With reference to FIG. 6 and continuing reference to the preceding figures, an exemplary intra-operative procedure employing the system 10 will now be described. For purposes of this example, the procedure is a biopsy. Having appropriately positioned the subject or patient 20 within the examination region 112 of the imaging apparatus 100, the robotic arm 190 holding the biopsy needle 192 in the needle holder portion 250 of its gripper 240 is initially positioned and/or arranged such that the needle 192 corresponds to the virtual needle 300 in the virtual planning view, i.e., such that the actual needle's tip registers with the entry point 302 and the actual needle's orientation matches the planned trajectory 306. Preferably, the robotic arm 190 automatically moves to its initial positioning and/or arrangement based upon position and orientation command signals generated by a program and derived from the virtual planning view constructed by the operator and maintained in the control console 150. That is to say, the interventionalist or other operator sends (from the control console or otherwise) the virtual planning view or data to a robot controller 400 which controls the movement of the robotic arm 190 into the desired position and orientation accordingly. The robot controller 400 is optionally a dedicated processor or processing unit, incorporated in the control console, or otherwise.

The interventionalist then physically uses the needle guide apparatus 200 to drive the actual needle 192, i.e., selectively advance and/or retract the needle 192 along its (the planned) trajectory during active CT fluoroscopy. That is to say, by manipulating the handle 266 of the guide apparatus 200, the interventionalist imparts a desired amount or degree of movement of the needle 192. This movement is measure by the feedback device 280 which generates a signal responsive or proportional thereto. The signal is communicated to a virtual view processing unit 410. The virtual view processing unit 410 updates the position of the virtual needle 300 in the virtual planning view display on the monitor 152 by advancing and/or retracting the virtual needle 300 along the planned trajectory 306 in accordance with the amount indicated by the feedback signal 281. Preferably, the virtual processing unit 410 continually updates the virtual planning view in this manner as the feedback signal varies due to manipulations of the needle guide apparatus 200. Additionally, the feedback signal may be used to update the real-time CT fluoroscopy image/view (not shown) as desired. This would be useful when the real-time view update period is large. The attenuated needle image would be shown with a virtual needle appendage, the size of which is representative of a difference between the needle depth from the prior CT fluoroscopy update and the position signal derived from the feedback device 280.

As with the robot controller 400, the virtual processing unit 410 is optionally a dedicated processor or processing unit, incorporated in the control console 150, or otherwise. Optionally, the advancement and/or retraction of the virtual needle 300 is indicated in the virtual view by: adjusting the depth-to-target reading; selectively switching portions of a line between a dashed, dotted or otherwise broken line which represents the remaining trajectory 306 not occupied by the needle, and a solid line representing the virtual needle 300; both of the foregoing; or otherwise as appropriate. In this manner, the interventionalist can visualize the progression of the procedure without having to continually image the patient 20, and hence, expose the patient 20 continually to the radiation beam 122.

As described, in addition to monitoring the progress of the procedure via the virtual view, the interventionalist may intermittently, as desired or upon demand, conduct an intra-operative imaging experiment 900 with the imaging apparatus 100 to obtain a real-time image which visualizes the actual procedure. Herein, these intra-operative images are referred to as the actual view. Insomuch as the imaging is intermittent, the radiation exposure to the patient 20 is less than the exposure that would otherwise be experienced if the patient 20 were being continually imaged. Preferably, the actual view is displayed on the monitor 152 alongside the virtual view. Accordingly, the interventionalist may consult the periodically updated actual view and reference it against the continually updated virtual view to ensure that the actual procedure is in fact progressing as indicated in the virtual view.

Having thus described the preferred embodiment(s), the invention is now claimed to be:

1. A system for inserting a medical device into a patient, the system including an imaging device scanning the patient to generate a volumetric image data set of the patient, a human readable device for displaying an image of the patient derived from said volumetric image data set, means for selecting a virtual trajectory defining a path for inserting the medical device into said patient, robotic means on said imaging device and movable into selected positions relative to the imaging device, and a guide apparatus disposed on the robotic means to direct movement of the medical device relative to the patient, the guide apparatus comprising:
   a connector portion coupling the guide apparatus with the imaging device at a distal end of the robotic means, and comprising a linear slider mechanism which restricts movement of the guide apparatus to a single linear path;
   a main body portion supported relative to the imaging device by the connector portion;
   a gripping area formed at a first end of the main body portion, the gripping area adapting the guide apparatus for manual gripping by an associated operator; and,
   a holding area formed at a second end of the main body portion, the holding area holding the medical device in an orientation suitable for motion relative to said patient along a selected linear path, the guide apparatus being operative to translate the medical device along said selected linear path in response to manual force applied by the associated operator at said gripping area during insertion of the medical device as restricted by the linear slider mechanism.

2. The system according to claim 1, wherein the imaging device is a CT scanner, an MRI scanner, a CCT scanner, a fluoroscope, a SPECT scanner, a PET scanner, or a combination of the foregoing.

3. The system according to claim 1, wherein the medical device is an ablation probe or a biopsy needle.

4. The system according to claim 1, wherein said means for selecting said virtual trajectory includes means for selecting a virtual target point in said image of the patient by identifying a first coordinate in said image of the patient, and means for identifying a virtual path extending from said selected virtual target point and the body of the patient.

5. The system according to claim 4, wherein said robotic means is adapted to move said guide apparatus into a position whereat said medical device is in an orientation suitable for motion relative to said patient along said selected linear path coincident with said virtual path extending from said virtual target point and the body of the patient.

6. The system according to claim 1, wherein the linear slider mechanism comprises a one of a linear slide joint and a prism joint.

7. The system according to claim 1, further including:
   a position feedback device provided on said connector portion of the guide apparatus for providing a feedback signal indicating a position of the guide apparatus relative to the patient; and,
   means for displaying an image of the medical device as it is physically moved relative to the patient based upon said feedback signal, together with said image of the patient and said virtual path.

8. The system according to claim 1, wherein the holding area is formed of an x-ray transmissive material.

9. The system according to claim 1, wherein the holding area includes a set of tweezers-like arm portions adapted to grip the medical device in a V-shaped groove formed by the arm portions.

10. A method of inserting a medical device into a patient, the method comprising:
    providing an imaging device scanning the patient to generate a volumetric image data set of the patient;

providing a human readable device for displaying an image of the patient derived from said volumetric image data set;

providing means for selecting a virtual trajectory defining a path for inserting the medical device into said patient;

providing robotic means on said imaging device and movable into selected positions relative to the imaging device;

providing a guide apparatus to direct movement of the medical device relative to the patient disposed on the robotic means, the guide apparatus including a connector portion coupling the guide apparatus with the imaging device at a distal end of the robotic means and comprising a linear slider mechanism which restricts movement of the guide apparatus to a single linear path; a main body portion supported relative to the imaging device by the connector portion; a gripping area formed at a first end of the main body portion, the gripping area adapting the guide apparatus for manual gripping by an associated operator; and, a holding area formed at a second end of the main body portion, the holding area holding the medical device in an orientation suitable for motion relative to said patient along a selected linear path, the guide apparatus being operative to translate the medical device along said selected linear path in response to manual force applied by the associated operator at said gripping area during insertion of the medical device as restricted by the linear slider mechanism; and, inserting the medical device into the patient by manually urging the guide apparatus towards said patient.

11. The method according to claim 10, wherein providing the imaging device includes providing a CT scanner, an MRI scanner, a CCT scanner, a fluoroscope, a SPECT scanner, a PET scanner, or a combination of the foregoing.

12. The method according to claim 10, wherein the medical device is an ablation probe or a biopsy needle.

13. The method according to claim 10,
wherein said means for selecting said virtual trajectory further comprises means for selecting a virtual target point in said image of the patient by identifying a first coordinate in said image of the patient, and means for identifying a virtual path extending from said selected virtual target point and the body of the patient, and the method further comprises moving the medical device and the guide apparatus while performing said scanning of the patient.

14. The method according to claim 13, further including using said robotic means to move said guide apparatus into a position whereat said medical device is in an orientation suitable for motion relative to said patient along said selected linear path coincident with said virtual path extending from said virtual target point and the body of the patient.

15. The method according to claim 10, wherein the linear slider mechanism comprises at least one of a linear slide joint and a prism joint.

16. The method according to claim 10, further including:
providing a position feedback device on said connector portion of the guide apparatus for generating a feedback signal indicating a position of the guide apparatus relative to the patient; and, displaying an image of the medical device as it is physically moved relative to the patient based upon said feedback signal, together with said image of the patient and said virtual path.

17. The method according to claim 10, including forming the holding area of an x-ray transmissive material.

18. The method according to claim 10, wherein the holding area includes a set of tweezers-like arm portions adapted to grip the medical device in a V-shaped groove formed by the arm portions.

19. A guide apparatus for assisting in medical procedures, the guide apparatus comprising:
a connector portion coupling the guide apparatus with an imaging device and comprising a linear slider mechanism which restricts movement of the guide apparatus to a single linear path;

a main body portion supported relative to the imaging device by the connector portion;

a gripping area formed at a first end of the main body portion, the gripping area adapting the guide apparatus for manual gripping by an operator; and, a holding area formed at a second end of the main body portion, the holding area holding a medical device in an orientation suitable for motion relative to a patient along a selected linear path, the guide apparatus being operative to translate the medical device along said selected linear path in response to manual force applied by the operator at said gripping area during an insertion of the medical device as restricted by the linear slider mechanism.

20. The guide apparatus of claim 19, wherein the holding area includes a set of tweezers-like arm portions for gripping the medical device in a V-shaped groove formed by the arm portions.

* * * * *